United States Patent
Manian et al.

(10) Patent No.: US 6,441,894 B1
(45) Date of Patent: Aug. 27, 2002

(54) OPTICAL AUTOFOCUS FOR USE WITH MICROTITER PLATES

(75) Inventors: Bala S. Manian, Los Altos Hills; David M. Heffelfinger, Oakland; Edward M. Goldberg, Redwood City, all of CA (US)

(73) Assignee: Biometric Imaging, Inc., Mountain View, CA (US)

(*) Notice: Subject to any disclaimer, the term of this patent is extended or adjusted under 35 U.S.C. 154(b) by 0 days.

(21) Appl. No.: 09/430,418

(22) Filed: Oct. 29, 1999

Related U.S. Application Data

(60) Division of application No. 09/245,782, filed on Feb. 5, 1999, now Pat. No. 6,130,745, which is a continuation-in-part of application No. 09/226,842, filed on Jan. 7, 1999, now abandoned.

(51) Int. Cl.[7] .................................................. G01J 1/00
(52) U.S. Cl. ...................................... 356/123; 356/244
(58) Field of Search ................................. 356/445–448, 356/244, 246, 73, 318, 417, 344, 436, 123, 124–133, 614–622; 250/458.1; 435/29; 422/63, 55–67; 369/44.13, 112

(56) References Cited

U.S. PATENT DOCUMENTS

| | | | |
|---|---|---|---|
| 5,355,215 A | 10/1994 | Schroeder et al. | 356/317 |
| 5,499,097 A * | 3/1996 | Ortyn et al. | 356/401 |
| 5,547,849 A | 8/1996 | Baer et al. | 435/7.24 |
| 5,556,764 A | 9/1996 | Sizto et al. | 435/7.24 |
| 5,589,351 A | 12/1996 | Harootunian | 435/29 |
| 5,663,794 A | 9/1997 | Ishizuka | 356/356 |
| 5,764,272 A | 6/1998 | Sarraf | 347/246 |
| 5,784,152 A | 7/1998 | Heffelfinger et al. | 356/73 |
| 6,081,487 A * | 6/2000 | Jacobowitz et al. | 369/44.13 |

OTHER PUBLICATIONS

"Optical Materials and Interference Coatings", Modern Optical Engineering by Warren J. Smith, c. 1990, Chapter Seven, pp. 187–197.
Brochure, "Position Sensing Detectors Theory of Operation", Photonics, Inc., Lake Forest, California 92630.
Brochure, "Metallic Neutral Density Filters", Newport.

* cited by examiner

*Primary Examiner*—Frank G. Font
*Assistant Examiner*—Tu T. Nguyen
(74) *Attorney, Agent, or Firm*—Thomas Schneck; David M. Schneck

(57) ABSTRACT

A method and apparatus for autofocus on a target layer contained within a microplate well is provided. The instrument is capable of optically sensing a reference point on the underside of a microplate. This reference point is then used to focus light onto a target layer within the microplate well, the target layer having a location that is in defined relation to the reference point. The reference point is either a surface of the bottom of the microplate well or is an optically detectable mark on the underside of the microplate. In an alternate embodiment, a light position sensitive detector is used to enable deterministic autofocus for a plurality of wells on a microplate.

13 Claims, 10 Drawing Sheets

OPTICAL AUTOFOCUS FOR USE WITH MICROTITER PLATES

CROSS-REFERENCE TO RELATED APPLICATION

This is a divisional application of application Ser. No. 09/245,782 filed Feb. 5, 1999, now U.S. Pat. No. 6,130,745, which is a continuation-in-part of application Ser. No. 09/226,842, filed Jan. 7, 1999, now abandoned

TECHNICAL FIELD

This invention relates generally to a method of focusing light for optical measurements into volumetric spaces and, more specifically, to an autofocus system for use with measurements in wells within microplates.

BACKGROUND ART

Numerous investigative assays use fluorescence to identify or enumerate a target of interest. Fluorescent detection has many applications in serology, cytology, microbiology, and histopathology. A chief advantage of using fluorescence is the low levels at which fluorescence can be detected, enabling highly sensitive tests. A second advantage with the use of fluorescence is that different fluorescent compounds have various different excitation and emission wavelengths. This allows for development of an assay of multiple targets in a single sample, with the assay for each target of interest associated with a different wavelength as a marker. An additional advantage is that fluorescence does not require the use of radioisotopes, resulting in reagents that are both safe to use and can be disposed of more easily.

One application of the use of fluorescent based assays is in the screening of compounds to identify potential pharmaceuticals. The process of drug discovery includes the screening of vast numbers of drug candidates made by combinatorial chemistry, requiring an extremely large number of assays. To simplify this process, assay procedures are often automated. Automation greatly increases screening throughput, allowing for more cost effective isolation of possible new drugs.

One method of automating the screening process involves introducing samples into a microplate well. These wells are often small, cylindrical receptacles arranged in rows in a rectangular array on a plastic sample plate. Commonly used microplates have 96, 384, or more wells per plate. Automated handling of these plates allows for higher throughput in screening samples in microplates.

Presently, assays using microplates and fluorescence detect emission in a two-dimensional reading of microplate wells. For example, U.S. Pat. No. 5,589,351 teaches a fluorescence analysis system that detects light transmitted from wells in a microplate. The light from a well is gathered and transferred to a reflector which sequentially directs light to a single detector. This system allows the sequential reading of rows of wells. The reading of wells is effected two dimensionally, with each well read as a unitary source of emitted light. This eliminates the ability of the assay to gather information on localized events within the well. U.S. Pat. No. 5,784,152 teaches another microplate reader that detects fluorescent emission. In this reader optical elements are included to enable tuneable detection to specific wavelengths. Detection is again effected in a two dimensional manner.

Three dimensional reading of microplate wells would allow more information to be gathered while using microplates. The targeted fluorescence often is localized on the bottom of microplate wells. The liquid in the microplate wells often contains additional unbound fluorescent reagents. In standard two-dimensional microplate fluorescent assays, detection of fluorescence on the bottom of a microplate well in a homogenous liquid is not possible. Fluorescent emission at the bottom of the well would be masked by the background fluorescence emitted from the unbound fluorescent compounds in the rest of the depth of the well. Simplified high throughput screens ideally would allow detection of the bottom layer in a well without removal of the unreacted fluorescent reagents.

To be able to detect fluorescence from the bottom layer of a microplate well requires the ability to automatically focus on a thin layer at the bottom of the well to excite fluorescent emission. This requires that the light source be able to focus on a 30 to 150 micron depth at the bottom of the microplate well. This focal depth would create a virtual capillary at the bottom of the well, a focal layer with the area of the well bottom but a depth of only 30 to 150 microns.

The geometry of microplates complicates attempts to focus on the bottom of microplate wells. A standard focal length would be possible if the plates were uniform to optical tolerance. However the location of the bottom surface of a microplate well is not uniform to 30 to 150 micron tolerances. To overcome this problem requires devising a method to precisely locate the bottom of a microplate well and focus on this location. In a high throughput system, this method must be rapid and accurate.

One known method of detecting a bottom layer in a microplate uses fluorescence detection to optically autofocus on a target layer within a microplate well. When the focal spot of laser light is below the well base top, minimal fluorescence will be detected. When the microplate is moved along the z axis of a microplate well (z axis is the longitudinal axis of the microplate well), the focal spot at some point begins to cross the well base top. The light from the focal spot will begin to excite fluorescent emission from some of the fluorescent compounds in the well as the focal spot enters the well. When the entire focal spot is above the well base top, a maximum fluorescent intensity is reached. FIG. 2 is a graph of the fluorescence intensity as the focal spot is moved into the well. The beginning of the maximum plateau of fluorescent intensity is a point where the location of the plate when the focal spot is entirely above the well base top. This has been used to refocus the beam within a microplate well. However, in practice this method has proved difficult to effect. The time required to use fluorescent graphing to determine focal spot placement within a well is not rapid enough for high throughput applications.

It is therefore an object of the invention to provide a method and apparatus capable of automatically focusing on a thin layer at the bottom of a microplate well. The focusing procedure should be rapid, accurate, and adaptable to fluorescence measurement in heterogeneous assays containing unbound fluorescent reagents. An additional object of the invention is to be able to use the focus method to determine the volume of liquid within the microplate well.

SUMMARY OF THE INVENTION

The above objects are achieved through a method and apparatus that uses a focused beam of light to optically sense a reference point on a microplate, such as the location of the top surface of the microplate well base, i.e. the surface defining the bottom of the well, and use this reference location to refocus the beam of light on a target within the microplate well that is positioned in a defined relation to the reference location. A scan of the target layer allows an assay of a thin layer within a microplate well without optical interference from non-target locations within the microplate well, particularly where fluorescence is used to identify target substances.

In a first embodiment, this method is achieved by focusing a beam of light toward the material interface occurring at an optically detectable reference surface on the underside of a microplate. The reference surface is then moved relative to the focal spot of the beam of light. As this movement occurs, specular reflection from the reference surface is collected and directed through a focal aperture onto a light detector where the intensity of the specular reflection is measured. A peak intensity will be measured when the focal spot of the beam of light is on the reference surface, allowing a maximal amount of light to be directed through a focal aperture and onto a detector. Once the location of the reference surface is known, this location can be used to relocate the beam of light onto a target layer in the microplate well if the target layer is in a known relation to the reference surface. Once the focal spot is relocated to the target layer, fluorescence is excited and detected using a scan of the target layer.

In an alternate embodiment the autofocus method, the focal aperture and detector are replaced with a position sensitive detector. Again a focal spot of a beam of light is directed to a reference surface on the underside of a microplate well. The reference surface is moved relative to the focal spot of the beam of light but the detector is kept stationary. As this movement occurs, the specular reflection from the reference standard is directed onto the position sensitive detector having a sensitive area large enough to image the reflected focal spot during its motion. The position sensitive detector measures both the intensity of the reflected light and the position of the reflected light on the detector. As in the first embodiment, the measurement of the maximum detected light intensity correlates to where focal spot is on the reference surface. When the light reaches the maximum intensity of measured specular reflection, the light will also be detected at a position on the position sensitive detector. This position on the position sensitive detector is the location when the focal spot is targeted onto the reference surfaces. Once this position on the position sensitive detector is known, it can be used as a deterministic indicator for finding the position of the reference surface at other locations on the microplate. As in the first embodiment, once the reference surface is located, it is used to reposition the focal spot onto a target layer which is subsequently optically scanned.

BRIEF DESCRIPTION OF THE DRAWINGS

FIG. 3c shows the autofocus optical elements of FIG. 1 being used to detect the well base top.

DESCRIPTION OF THE PREFERRED EMBODIMENTS

Figure 1:
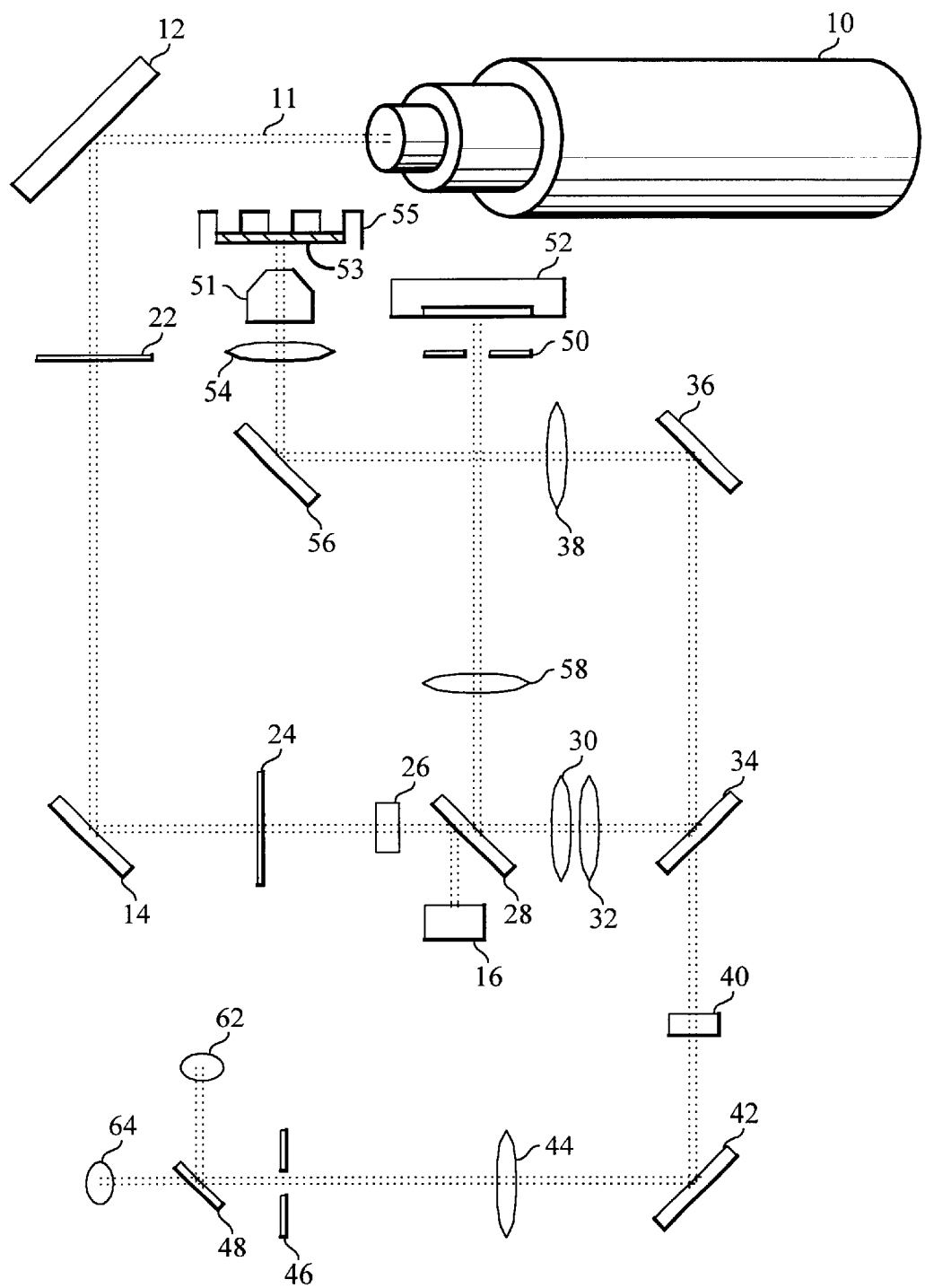
FIG. 1 shows the optical elements of a fluorescence spectrometer with autofocus capability in accordance with the present invention.
Figure 2:
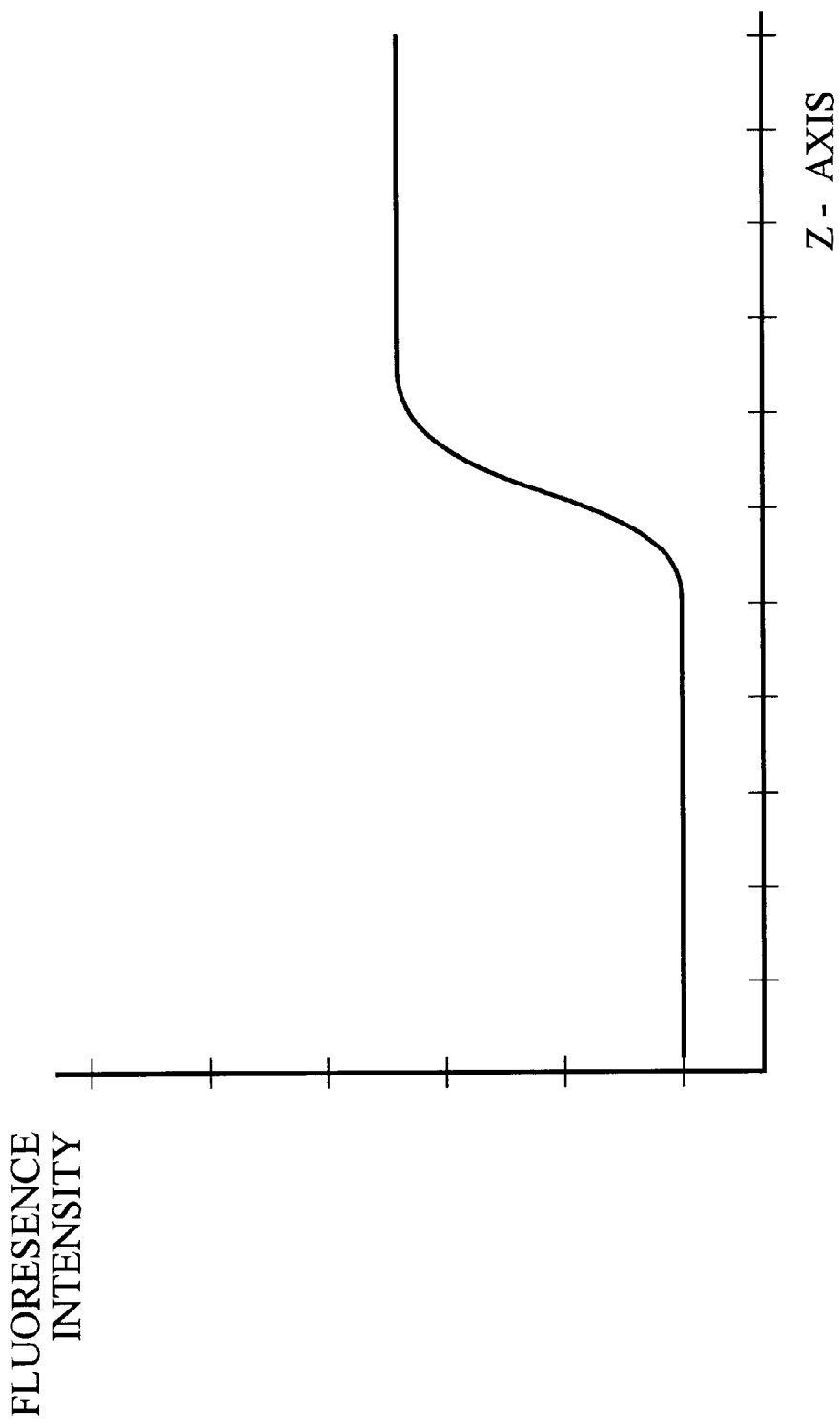
FIG. 2 shows a graphic result of a prior art focusing method.

With reference to FIG. 1, a laser 10 produces laser beam 11. In the preferred embodiment, a helium-neon laser is used. This laser can produce coherent light at a wavelength of 633 nm. The use of this wavelength light allows for optimal detection of fluorescent target compounds in biological samples since the light absorbance of typical biological samples is below this wavelength, hence autofluorescence from said samples is minimized. Laser light 11 is directed by a first steering mirror 12 through a first shutter 22. The light next is directed by second steering mirror 14 through a second shutter 24. Shutters 22 and 24 are included to comply with laser safety requirements. After passing through the second shutter 24, the laser light next passes through laser line filter 26. Laser line filter is included to suppress the plasma tube light but allow the laser light to be transmitted. This is needed because the plasma light interferes with the fluorescent light to be collected. The laser light passes through laser line filter 26 onto beam splitter 28. Beam splitter 28 reflects some of the light into laser power sensor 16. Power sensor 16 continuously monitors the power of the laser and is able to detect if the light power output is below the specification requirements. Additionally monitoring the light power would allow for normalizing the light output. The laser light that is not deflected by beam splitter 28 is transmitted through the beam splitter and through positive contractor lens 30 and negative contractor lens 32. These lenses are used to shape the size of the laser light beam to produce the required focal spot size on the target microplate well. The laser light is then directed by laser dichroic splitter 34 onto oscillating galvo mirror 36. The movement of oscillating galvo mirror 36 creates movement of the laser light along one axis. The light is directed by oscillating galvo mirror 36 through galvo relay lens 38 and is directed by relay fold mirror 56 through objective relay lens 54 which focuses the light. The purpose of the galvo relay lens 38 and objective relay lens 54 is to image the laser illuminated center of the galvo on the entrance pupil of the objective lens. In the preferred embodiment, relay fold mirror 56 directs laser light 11 in a direction such that the light is orthogonal to the plane in which the light had been previously directed. The light next passes through objective 51 and onto the target microplate well base bottom 53.

This optical system allows for the two dimensional scan of the well base bottom 53. The galvo mirror 36 enables movement of the focused light along one axis. The stage (not pictured) for holding microplate 53 enables movement of the focused light along another axis. Incremental movement of the stage creates raster line scan of the bottom of a microtiter plate. A raster line scan of the plane of a thin target layer contained in a microplate well enables detection of fluorescence over a large surface area with a limited depth of field.

Once the light is directed through well base bottom 53 and into microplate well 55, light can be collected from two sources depending on where the focal spot of the light is targeted.

First, some of the laser light can be collected from specular reflection from some surface where there is a material transition, such as the transition from air to glass/plastic at well base bottom 53. This light will be reflected back through objective 51 and objective relay lens 54 and will be directed by relay fold mirror 56 through galvo relay lens 38. The reflected light is then directed by galvo mirror 36 onto laser dichroic splitter 34. Because this light is reflected light it is the same wavelength as the original laser light 11 and will not pass through laser dichroic splitter 34 but instead will be directed through negative contractor lens 32 and positive contractor lens 30 onto beam splitter 28. Beam splitter 28 directs the specularly reflected laser light through focus sensor lens 58 and towards aperture 50. The reflected light that is focused will not be stopped by the aperture 50 and will be detected by sensor 52. This is further explained in relation to FIGS. 3a, 3b, 3c and 3d.

Second, the laser light can be focused into the interior of a well 55 on microplate 53. Contained within the well are fluorescent compounds that are excited by light of the wavelength of laser light 11. When the laser light is directed onto the fluorescent compounds in the interior of microplate well 55, fluorescent light of a known wavelength will be produced. In the preferred embodiment, the fluorescent compounds are Cy5™ and Cy5.5™, fluorophores that are available from Amersham Life Sciences, Inc. of Arlington Heights, Ill., and which emit fluorescent light maximally at 670 nm and 698 nm respectively. This light is emitted and some will enter into objective 51 and pass through objective relay lens 56 onto relay fold mirror 56. The fluorescent emitted light is directed through galvo relay lens 38 and onto galvo mirror 36 which directs the fluorescent light onto laser dichroic mirror 34. The laser dichroic splitter 34 is selected to reflect light of the wavelength of the laser light but allow through light of the wavelength of the fluorescence emission. The fluorescent light that passes through laser dichroic splitter 34 then passes into long pass filter 40. Long pass filter suppresses any laser light that passed through laser dichroic splitter 34. In the preferred embodiment, the long pass filter 40 passes light that has a wavelength above 645 nm and suppresses lower light wavelengths. The fluorescence light then is directed by fold mirror 42 through spatial filter lens 44 which focuses the fluorescent light through aperture 46. The aperture blocks rays of the fluorescence emission that originate outside the collection volume of interest. The fluorescence light that passes through aperture 46 is then directed by fluorescence dichroic filter 48 which splits the light into two channels. Light below 680 nm is reflected by fluorescence dichroic filter 48 onto photomultiplier tube 62 which detects fluorescent light. Light above the 680 nm cut off passes through fluorescence dichroic filter 48 and is detected by photomultiplier tube 64.

Homogeneous assays require limiting the depth of field of the scan of a microplate well to a thin target layer contained within the microplate well. Target cells or fluorescent beads are often located at the bottom of a microplate well. This is a result either of binding of the target to some compound associated with the well bottom or is the result of gravitational settling. Unreacted fluorescent compounds that remain in solution ordinarily would prevent the localized detection of fluorescence from a specific target layer within a microplate well. The background fluorescence from unreacted fluorescent compounds would effectively make the fluorescence from a target layer in a microplate well undetectable. It is necessary to locate the target layer in the microplate well and focus a beam of light on this location. This prevents the illumination and fluorescent emission from the area of the well that is not the target. The focus depth required ranges from 30 to 150 microns from the bottom surface of a microplate well. Because microplates are not designed to be optically flat to these tolerances, there must be some method of automatically sensing a reference point that has a known relation to the target layer.

Figure 3A:
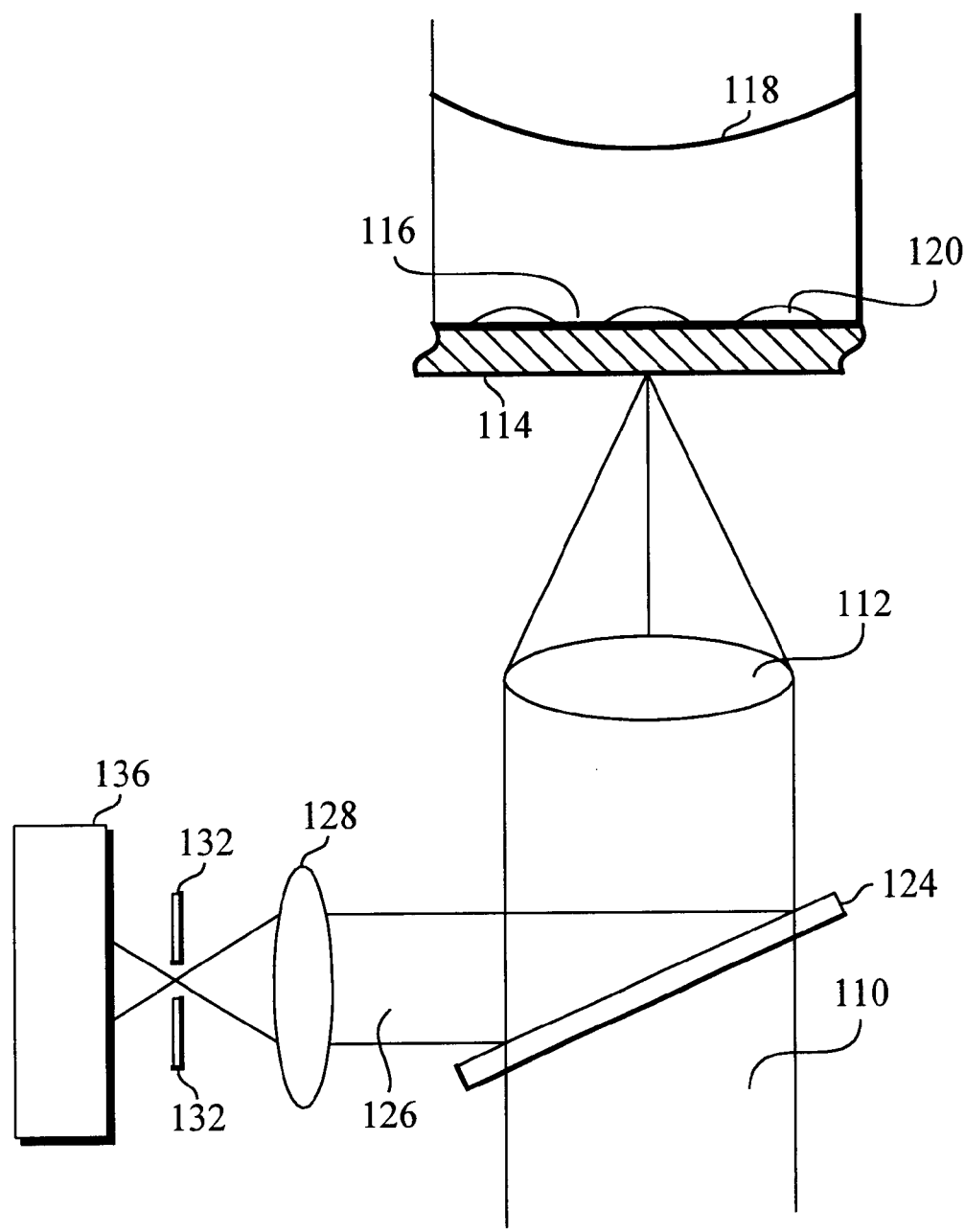
FIG. 3a shows the autofocus optical elements of FIG. 1 being used to detect the well base bottom.
Figure 3B:
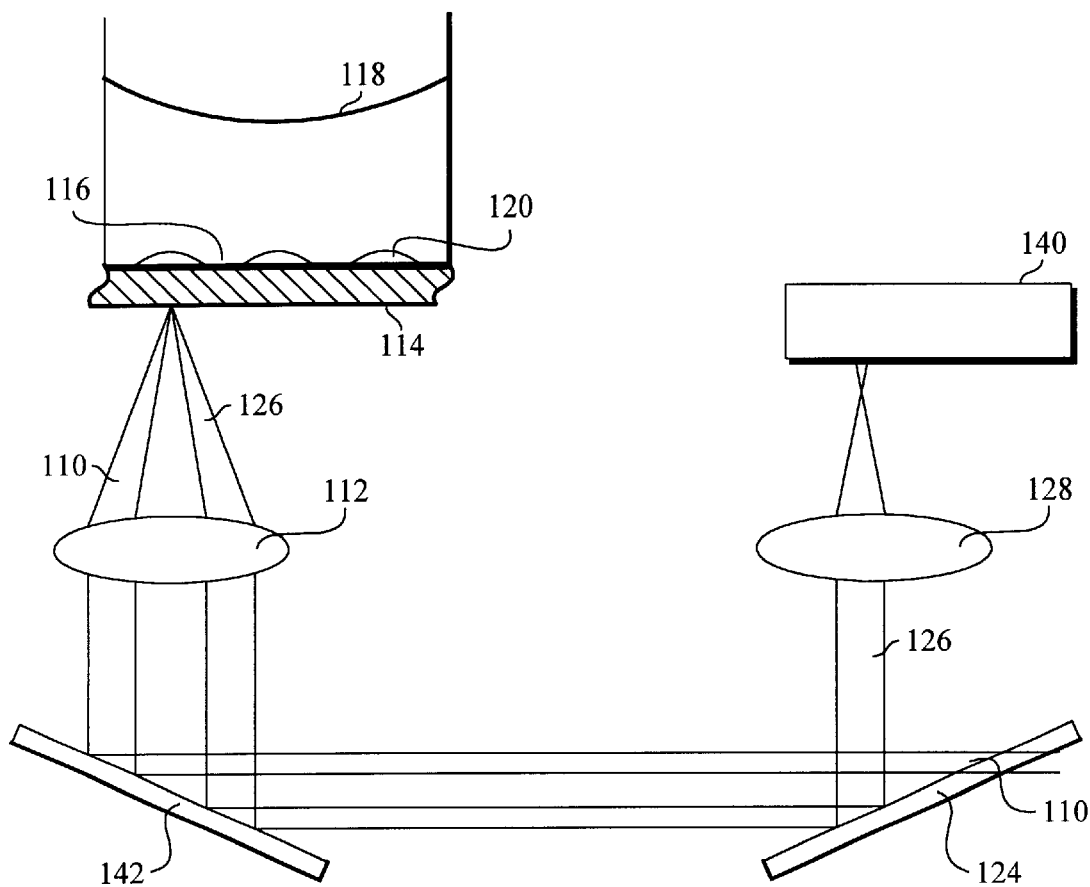
FIG. 3b shows the optical system of FIG. 3a using an alternative detector.
Figure 36:
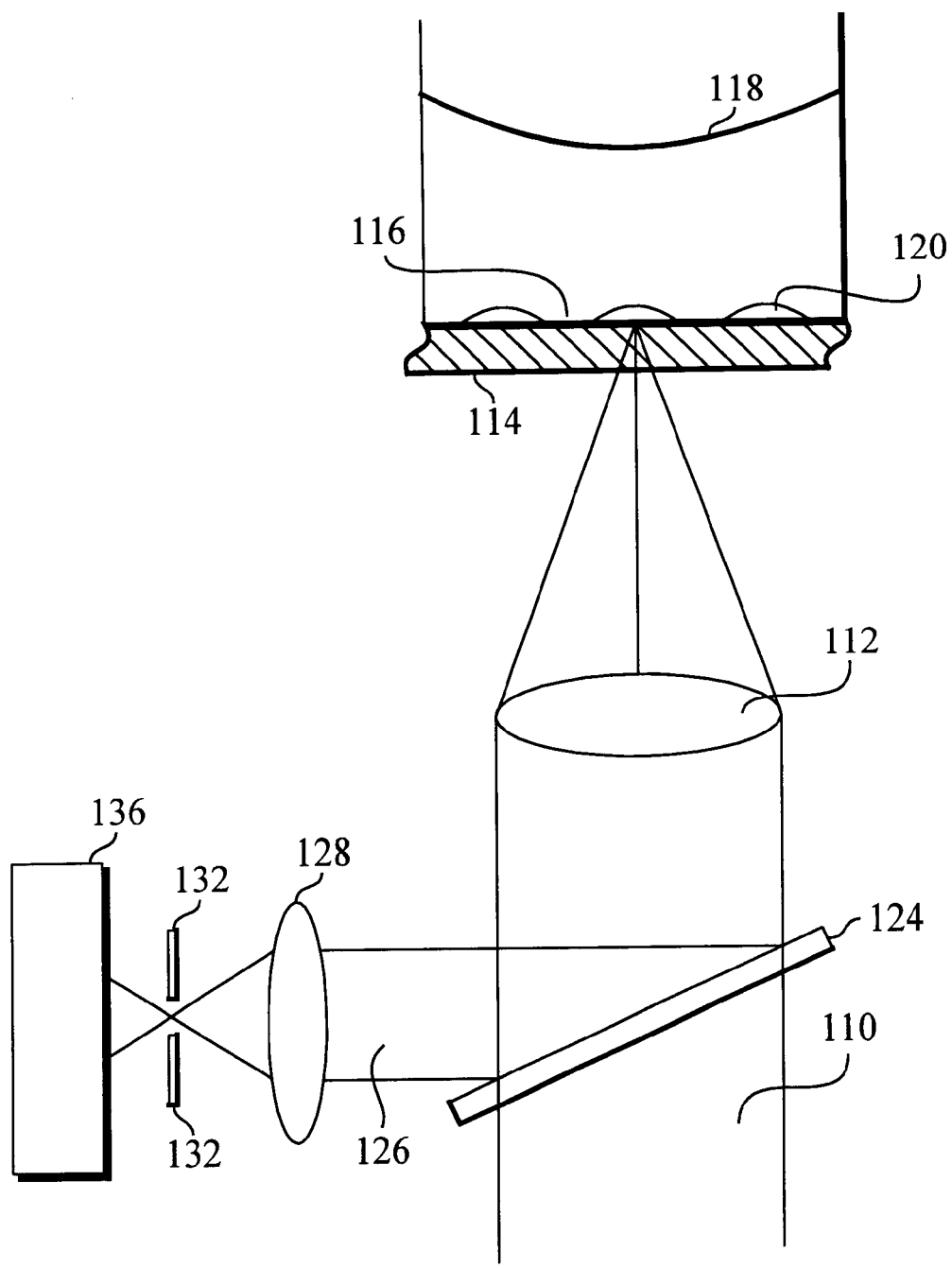
Figure 3D:
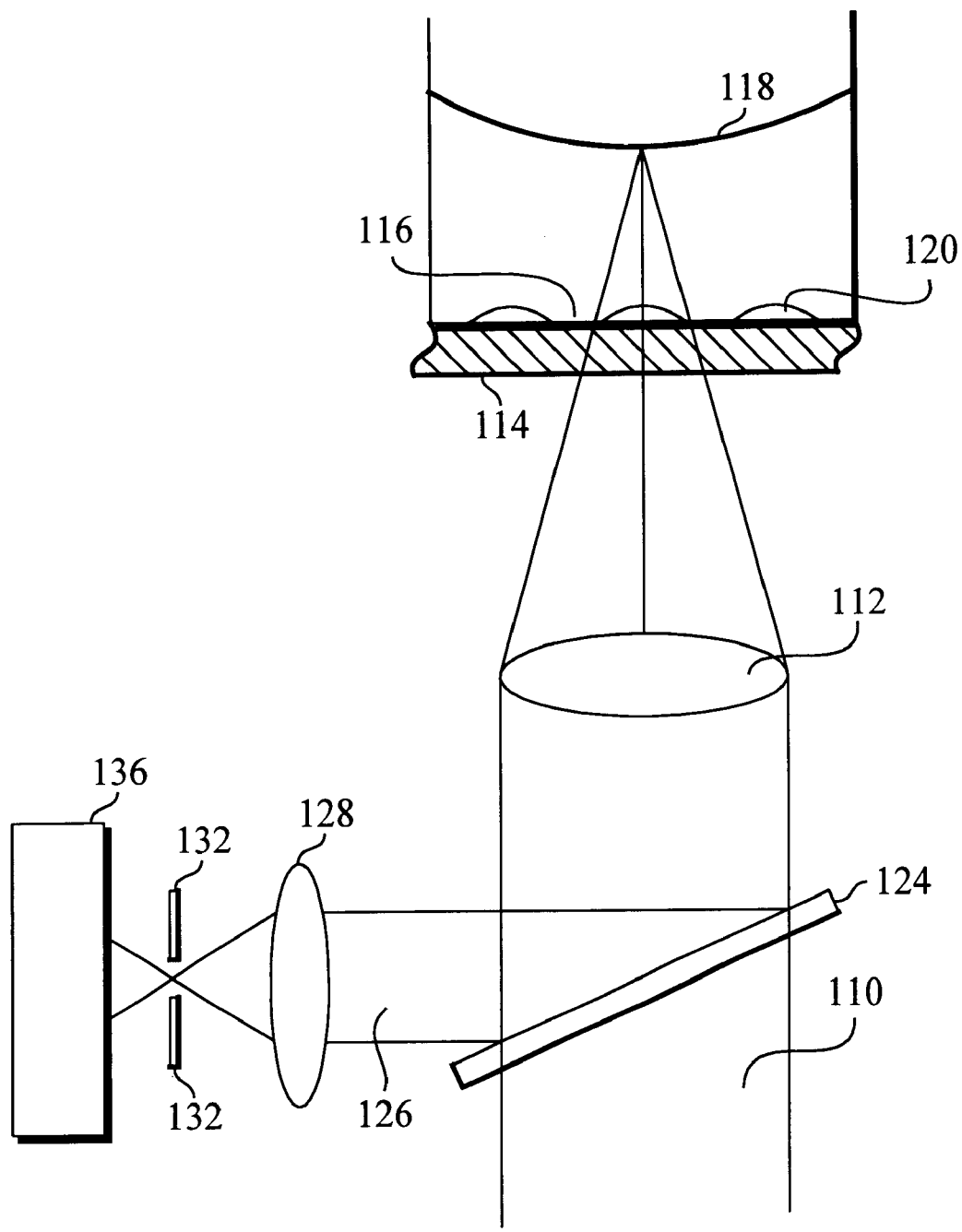
FIG. 3d shows the autofocus optical elements of FIG. 1 being used to detect the surface of liquid within a microplate well.
Figure 4:
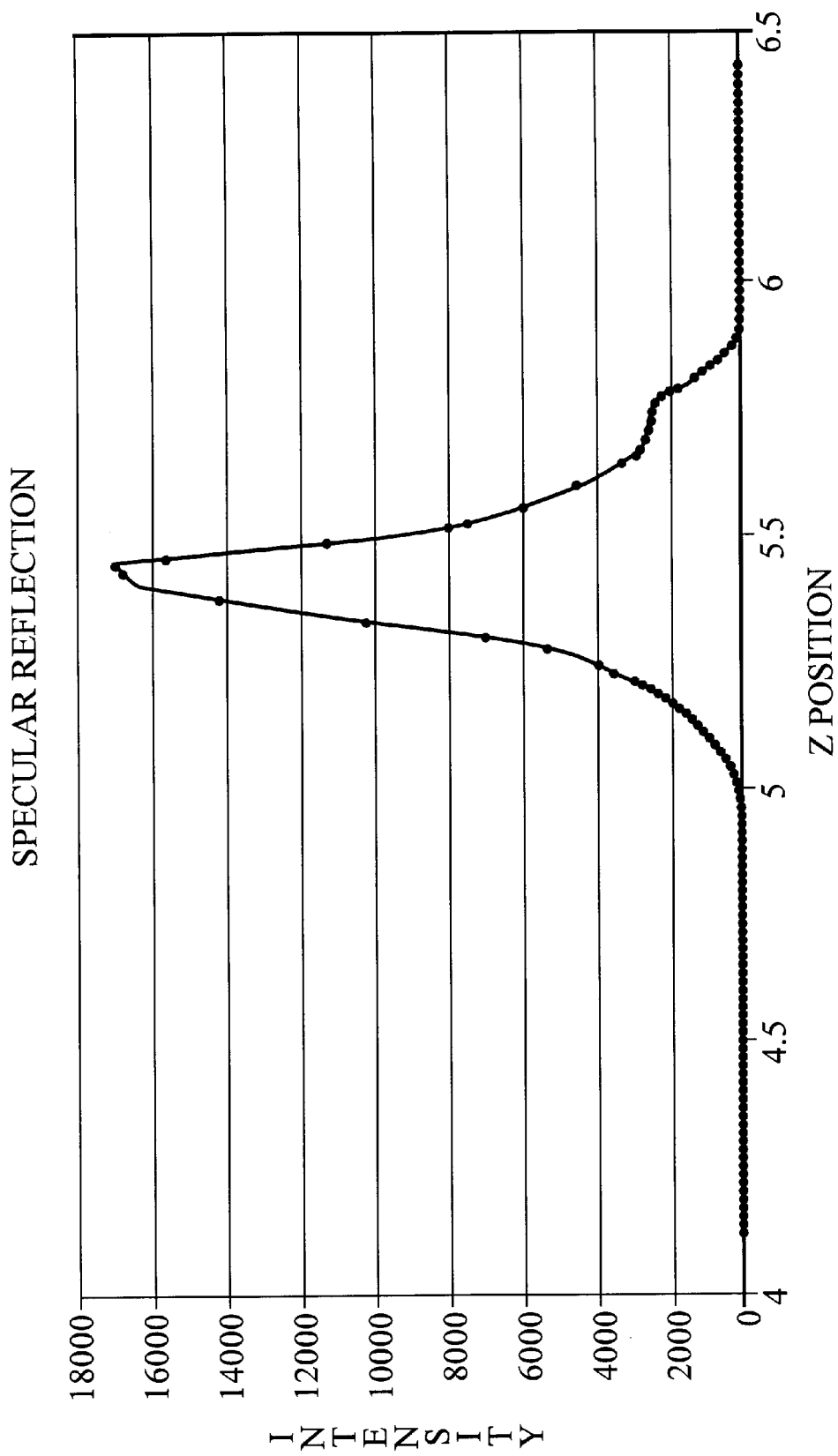
FIG. 4 shows a graph of the specular reflection of light as the bottom of a microplate well is moved along the longitudinal axis of the well relative to a focal spot of light beam.

A principal embodiment of the optical autofocusing is shown in FIGS. 3a, 3c, and 3d. FIG. 3a shows the autofocusing elements of FIG. 1 used to detect the well base bottom 114 of a microplate well base. A microplate well is formed by walls extending downward from the top of the microplate. The base of the well is formed by a layer of transparent glass or plastic material. A well base top surface of the well base faces the open top end of the wells. A well base bottom surface of this well base faces down from the open underside of the microplate. The target cells 120 have gravitationally settled to the bottom of the liquid in a microplate well. The layer of plastic or glass that comprises the well base has a well base top 116 where the target cells have settled and well base bottom 114. A beam of laser light 110 is directed through beam splitter 124 and is focused by lens 112 into a focal spot. This focal spot is directed toward well base bottom 114. Some of the light that is directed toward well base bottom 114 will be reflected by specular reflection back towards lens 112. This light will be directed by beam splitter 124 through focus sensor lens 128 and toward focus sensor aperture 132. Focus sensor aperture acts as a stop for light that is not focused. By changing the size of this aperture the size of the focal spot can be matched. The light that passes through focus sensor aperture 132 is detected by focus sensor 136. This focus sensor could be a photodiode or other device that measures the intensity of the reflected light. To determine the location of well base bottom 114, the microtiter plate is moved along the longitudinal axis of a microplate well. This results in the movement of the focal spot along this axis. When the beam's focal spot is not on well base bottom 114, the specular reflection from well base bottom 114 will be more broadly scattered. This scattered light will be stopped by focus sensor aperture 132 resulting in less light detected by detector 136. In contrast, when the waist of the focused beam is on well base bottom 114 the specular reflection from well base bottom 114 will be less scattered. This results in more light passing through focus sensor aperture 132 where the light is detected by detector 136. FIG. 4 graphs the intensity of detected light as the well base bottom 114 is moved along the z axis relative to the waist of the a focused light beam. At position 5 on the z axis, the beam's focal spot is below the well base bottom of the plate and little light is focused through the focus sensor aperture. As the microplate is moved along the z axis and the focal spot of the beam comes closer to the well base bottom, more specular reflection from the well base bottom is detected. Near position 5.4 on the z axis, the maximum intensity of specular reflection is reached. This occurs when the focal spot of the beam of light is focused on well base bottom 114. As the microplate is moved along the z axis, the intensity of specular reflection decreases as the focal spot of the beam moves into the interior of the well base. Using this method, the location along the z axis where the focal spot of the beam is focused on well base bottom 114 can be determined. This location is then used as a reference point for relocating the focal spot of the light beam to a target layer in the microplate well. The distance between well base bottom 114 and well base top 116 is the thickness of the plastic or glass material that comprises the well base. The dimension of this thickness is available from the manufacturer of the microplate. The waist of the light beam can be moved to just above well base top 116 to locate cellular targets 120. The optical system can then effect a scan of the target layers.

The autofocus method described in relation to FIG. 3a requires that the longitudinal axis of the focused light beam be substantially perpendicular to the well base bottom 114 of the microplate well bottom. This is effected by centering the galvo relay mirror 36 and holding the mirror stationary. The light is then focused by lens 112 perpendicular to the well base bottom 114.

In an alternate embodiment seen in FIG. 3b, substitution of the detector allows for additional features in the autofocus system. In this embodiment, laser light 110 passes through beam splitter 124 and onto galvo relay mirror 142. In this embodiment, galvo relay mirror 142 is not centered but is moved to a fixed position such that laser beam 110 is directed at a non-perpendicular angle in relation to well base bottom 114 and is again held stationary. Thus laser light 110 is directed through lens 112 and onto well base bottom 114 such that the longitudinal axis of the laser light is not perpendicular to well base bottom 114 but instead is directed at a non-right angle in relation to well base bottom 114. Laser light 110 will be reflected by well base bottom 114 by specular reflection producing reflected light 126. This light will pass through lens 112 and be directed by galvo relay mirror 142 onto beam splitter 124. Because the reflected light 126 is the same wavelength as the original laser light 110, the light will not pass through beam splitter 124 but instead is directed through focus sensor lens 128 onto position sensitive detector 140.

One example of a position sensitive detector (PSD) is a silicon photodiode that produces an analog output directly proportional to the position of a light spot on the optically sensitive strip of the detector. This allows for simultaneous measurement of light intensity and light position on the detector. When the light strikes the photodiode, a photoelectric current is generated. The photoelectric current generated by the incident light is an input current that is divided into two output currents. The distribution of the output currents on the optically sensitive strip indicates the light position on the detector. The sum of the output current indicates light intensity.

The measurement of light intensity is used in the same manner as seen in FIG. 3a. To determine the location of a surface on the underside of a microplate, the well base bottom 114 is moved relative to the beam's focal spot. This will cause the focal spot to move from below well base bottom 114 onto well base bottom 114. When this occurs the intensity of light detected by the PSD will increase as the increasingly small light spot allows more light to impinge within the width of the photosensitive element on the PSD. At the light intensity peak the waist of the beam will be focused onto well base bottom 114. This can again be used as a reference location for relocation of the waist of the beam to a target layer within the microplate well. As the focal spot moves from below well base bottom 114 onto this surface and then into the well base, the intensity of the reflected light again forms a Gaussian curve with a similar shape to the curve shown in FIG. 4. At the peak of the curve the intensity of reflected light is at a maximum indicating that the focal spot is on well base bottom 114.

The width of the photosensitive strip on the PSD 140 determines what optical configuration is used with PSD 140. If the width of the strip is very narrow, an aperture may be placed between focus sensor lens 128 and PSD 140. The aperture functions as a stop for unfocused light, producing a Gaussian curve as the focal spot moves onto and off of well base bottom 114. In contrast if the width of the photosensitive strip on the PSD is wide, the PSD 140 could be used without focus sensor lens 128. The intensity of the light is measured as the specular reflection becomes collimated when focused on well base bottom 114.

In addition to intensity of light, the PSD also measures the location of the light along the photo-sensitive length of the PSD. Since the light is directed at a non-right angle in relation to well base bottom 114, moving of well base bottom 114 relative to the waist of the beam of light alters where the center of the focused beam strikes under surface 114. This in turn alters where the reflected light impinges along the length of the photosensitive length of the PSD. Thus the light moves along the length of the PSD as the well base bottom 114 is moved relative to the focal spot. The point where the focal spot is on well base bottom 114 corresponds to light impinging on one location on the PSD. Light moves away from this location in one direction along the PSD when the focal spot is moved below well base bottom 114 and light moves in the other direction away from this location when the focal spot is moved above well base bottom 114.

Using the PSD for focusing on a target layer within a microplate well requires first measuring both intensity of reflected light and the position of reflected light on the PSD as the microplate is moved along the z-axis. The peak intensity corresponds to the location where the focal spot is on the well base bottom. This requires a range of movement along the z-axis for one microplate well. Once these measurements are taken for one microplate well, the location along the length of the PSD that corresponds to the measurement for peak light intensity is known. Once this location is known it becomes a reference measurement that allows deterministic autofocus for other wells on the microplate. For each other well on the plate, a single measurement of specular reflection along the z-axis will correspond to a location along the photosensitive length of the PSD. This location along the PSD can be compared to the position along the PSD known to be the intensity peak. This indicates both the direction and amount the bottom needs to be moved to focus the waist of the beam on the well base bottom.

Figure 8:
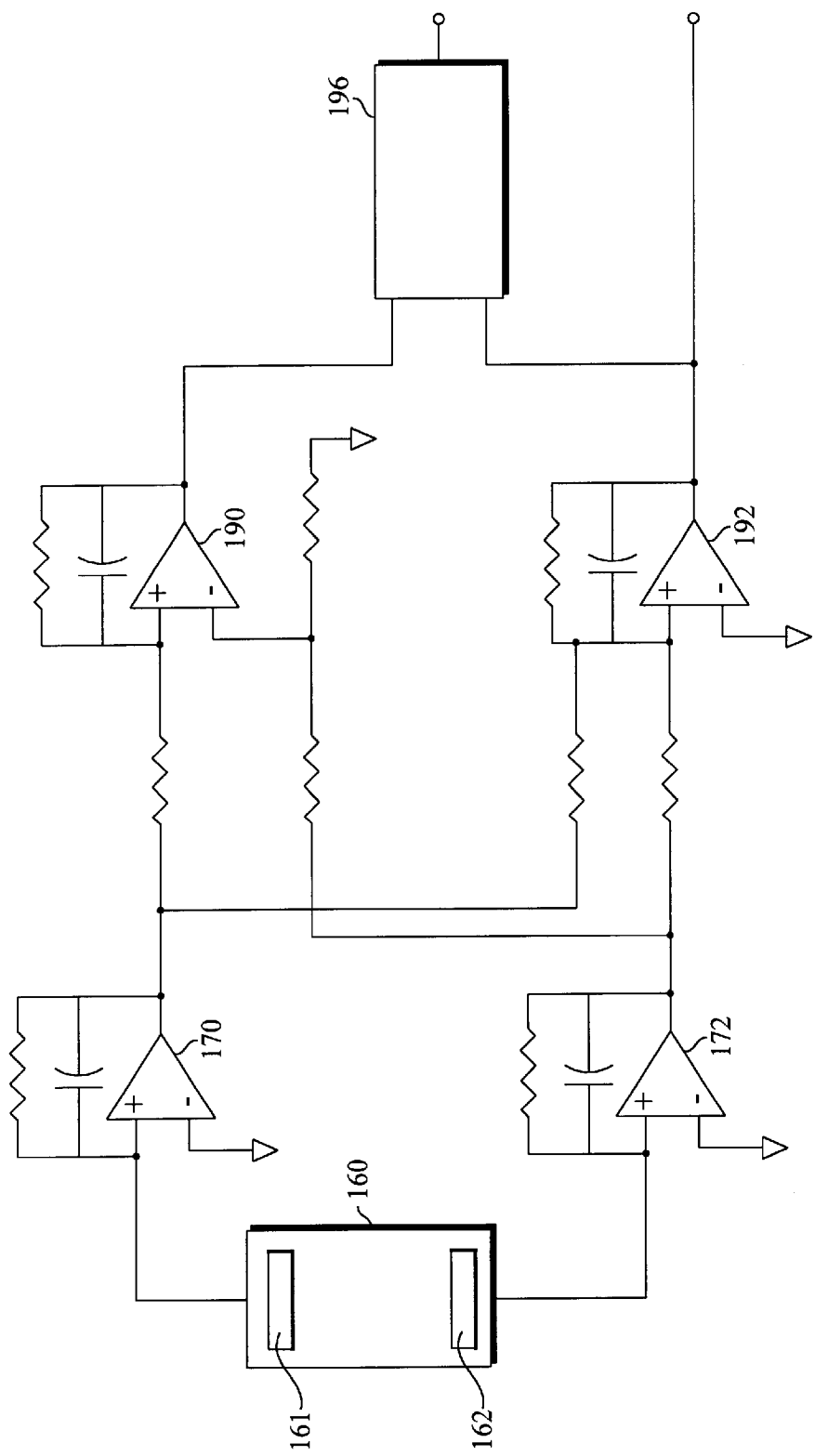
FIG. 8 depicts a circuit diagram of the circuit used with the position sensitive detector of FIG. 3b.

A circuit is used with the PSD to effect the relevant measurements. With reference to the optical position sensing detection circuit of FIG. 8, light strikes a silicon photodiode 160 that provides an analog output directly proportional to the position of a light spot on the detector's optically active area. Output signals are taken at the electrodes 161 and 162. The output from electrode 161 is fed to the operational amplifier 170 while the output from electrode 162 is fed to operational amplifier 172 in a path parallel to op amp 170. The two operational amplifiers reside in parallel symmetric paths which are cross coupled. Op amp 170 is cross coupled to an input of op amp 192 which also receives an input from op amp 172. Op amp 190 is cross coupled to op amp 172 which also receives an input from op amp 170. In this way, signals are both added and subtracted such that in the upper channel, by appropriate inputs of op amp 190, the output of op amp 190 is a subtractive signal, X1−X2, while in the lower channel, the output of op amp 192 is an additive signal, X1+X2. These two combined signals are fed to an analog divider 196 which takes the ratio of the two signals as X1−X2/X1+X2. The output of op amp 192, X1+X2 gives the intensity measurement. The output of analog divider 196 gives the position of incident light on the detector normalized for light intensity.

Figure 5:
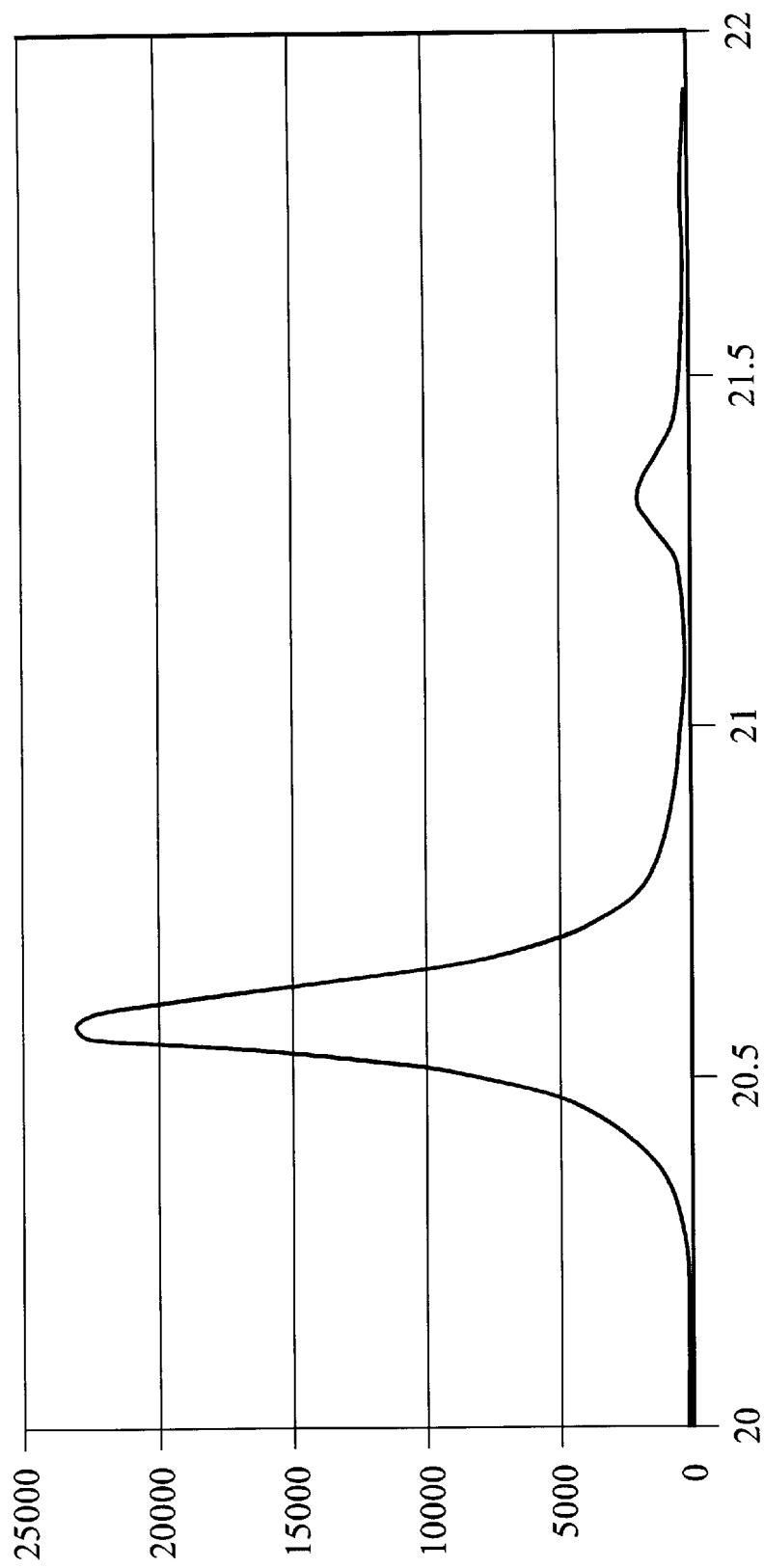
FIG. 5 shows a second graph of the intensity of reflected light as the base of a microplate well is moved along the longitudinal axis of the well in relation to a focal spot of light beam.

FIG. 3c illustrates an alternate optical autofocus method to locate a target layer in a microplate well. In this method the focal spot is directed toward well base top 116. As in FIG. 3a, the specular reflection from this surface is collected and focused through focus sensor aperture 132 and detected by focus sensor 136. As in FIG. 3a, the focal spot is moved along the z axis. Also as in FIG. 3a, the maximum intensity of specular reflection will occur when the focal spot of the beam is located at well base top 116. This surface again can be used as a reference point for the location of the layer containing the target of interest. FIG. 5 illustrates the intensity profiles detected from the well base bottom and well base top as a well base is moved relative to a focal spot of a beam of light. The larger intensity peak at about 20.5 is the specular reflection from the well base bottom. The smaller second peak at about 21.4 is the reflection from the well base top. This second peak is much smaller than the first peak, indicating much less specular reflection from the well base top. This is a result of the lower index of reflection.

The lower index of reflection is a result of the different transitions from one material to another. The amount of light produced by specular reflection is determined by the formula:

$$I = (N-N')^2/(N+N')^2$$

N is the index of reflection of the first material that light passes through.

N' is the index of reflection of the second material that light passes through.

From this formula it can be seen that specular reflection will be greater for transitions between materials with indexes of refraction that are further apart. The well base bottom of the microplate well base is a transition from air, with an index of reflection of 1, to plastic or glass, with an index of reflection of 1.47 to 1.5. The relatively large difference between these two indexes of reflection creates the specular reflection as seen in the intensity peak at 20.5 seen in FIG. 5. In contrast the well base top of the microplate well base is a transition from plastic, with an index of reflection of 1.47, to a liquid contained within the well, at an index of refraction of 1.33. The relatively small difference between the indexes of reflection creates the much smaller intensity peak at 21.4 seen in FIG. 5. In some microplates the optical quality of the materials used is not sufficient to resolve the intensity peak from the specular reflection from the well base top.

Coatings may be added to a surface to alter the index of reflection and make detection of the upper surface by specular reflection feasible. For example, the well base bottom could be coated with a coating to decrease reflection. The antireflection coating is added to the well base bottom by vacuum evaporation deposition. Examples of compounds used for antireflection coatings include magnesium fluoride and lanthanum trifluoride. Alternatively the upper surface of the well could be coated with a coating to increase reflection. Compounds to increase reflection include metallic neutral density coatings which can be vacuum deposited on the well base top at the desired thickness to give the desired amount of reflection.

Figure 6:
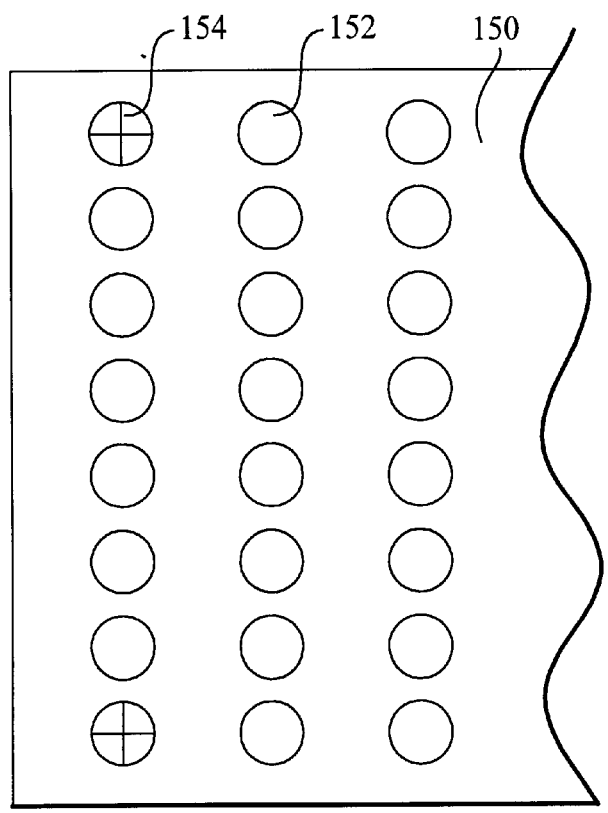
FIG. 6 shows a section of a microplate with optically detectable registration marks.

Another method to optically focus on a target layer in a microplate well uses optically detectable features added to the underside of a microplate that function as a reference point for the location of the thin layer in a microplate well. FIG. 6 shows a portion of the bottom of microplate 150 having these features. Optically detectable well 154 has an optically detectable feature enabling precise localization of the of the well base top. Once this surface has been detected it is used as a reference point for detecting the upper surface of well 152 that does not have the optical features.

Figure 7:
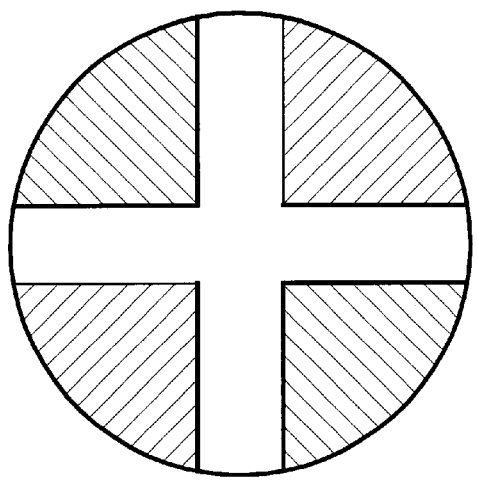
FIG. 7 shows optically detectable registration marks of a microplate well bottom used in the microplate of FIG. 6.

An example of the optically detectable registration marks is shown in FIG. 7. FIG. 7 shows the upper surface of a well bottom that has been physically altered to be optically detectable. The shaded sections indicate areas of the surface that have been roughened to decrease reflection from the surface. The unshaded areas indicate areas that have not been roughened and will have comparatively higher amounts of specular reflection. When the focal spot is focused on the optically altered bottom surface and scanned across the surface there will be a sharp transition as the focal spot moved from the rough area of the bottom to the non-rough area of the bottom of the plate. When the spot is unfocused the transition will be less sharp.

The optical reference marks can be located on the well base bottom, on the well base top, or at another location on the underside of a microplate as long as this location has a defined relation to the location of the well base. The optically detectable reference may be the scribe marks described or could alternatively be bar code indicia, or patterned reflected coating (such as the neutral density coatings previously described).

FIG. 3d shows the autofocusing elements of FIG. 1 used to detect the liquid surface 118. Once the well base top 116 of the bottom of the well is located, the focal spot of the light beam can be moved along the z axis toward the top of the well. When the focal spot is proximate to the liquid surface, specularly reflected light can be detected by focus sensor 136. As with the other surfaces, as the focal spot is moved toward surface 118 the intensity of the reflected light increases to a maximum point when the focal spot is located at liquid surface 118. Once the location of the liquid surface 118 and microplate well base top 116 are known, the volume of liquid in the well can be calculated if the geometry of the well is known.

We claim:

1. A container for analysis of a target layer using an optical system, the container comprising:
   a rigid, transparent surface on said container; and
   at least one registration mark positioned in a defined location on said surface, wherein said at least one registration mark is optically detectable by detection of specular reflection, wherein said at least one registration mark is adaptable for use as a reference location for determining the position of said target layer within the container.

2. The container of claim 1, wherein the at least one registration mark is a patterned reflective coating located on the surface.

3. The container of claim 1, wherein the at least one registration mark is a pattern of scribe marks of greater and lesser reflectivity located on the surface.

4. The container of claim 1, wherein the at least one registration mark is bar code indicia located on the surface.

5. A microplate for detecting the position of a target layer using an optical system, comprising:
   a block having a plurality of depressions forming wells in an array within said block, each well having a base;
   a rigid transparent layer forming a bottom surface of said wells in known relation to the base of each well; and
   at least one optically detectable registration mark positioned on an underside of said microplate in defined relation to a well base and adaptable for use as an optical reference location for determining the position of said target layer within the microplate wells.

6. The microplate of claim 5, where the at least one registration mark is a patterned reflective coating located on the underside of the microplate.

7. The microplate of claim 5, where the at least one registration mark is a pattern of scribe marks of greater and lesser reflectivity located on the underside of the microplate.

8. The microplate of claim 5, where the at least one registration mark is bar code indicia located on the underside of the microplate.

9. The microplate of claim 5, wherein said at least one registration mark is located on at least one well base bottom.

10. The microplate of claim 5 wherein said at least one registration mark is located on at least one well base top.

11. A container for analysis of a target layer using an optical system, the container comprising:

a base including an upper rigid, transparent surface and a lower rigid transparent surface on said container; and at least one registration mark positioned on one of said surfaces in a defined location relative to said other surface, wherein said at least one registration mark is adaptable for use as a reference location for determining the position of said target layer within the container.

12. The container of claim 11 wherein said registration mark is positioned on said upper surface.

13. The container of claim 11 wherein said registration mark is positioned on said lower surface.

* * * * *